United States Patent [19]

Lazar et al.

[11] 4,267,840
[45] May 19, 1981

[54] ELECTROSURGICAL GROUNDING PAD

[75] Inventors: Lawrence S. Lazar, Morristown; Robert F. Wittemann, New Brunswick, both of N.J.

[73] Assignee: Johnson & Johnson, New Brunswick, N.J.

[21] Appl. No.: 1,503

[22] Filed: Jan. 8, 1979

[51] Int. Cl.³ .............................................. A61B 17/39
[52] U.S. Cl. ............................... 128/303.13; 128/798
[58] Field of Search ................................. 128/639-641, 128/644, 303.13, 783, 798, 802, 803

[56] References Cited

U.S. PATENT DOCUMENTS

| | | | |
|---|---|---|---|
| 1,989,282 | 1/1935 | Kimble | 128/798 |
| 3,542,010 | 11/1970 | Love | 128/644 |
| 3,942,517 | 3/1976 | Bowles et al. | 128/641 |
| 3,989,035 | 11/1976 | Zuehlsdorff | 128/641 |
| 3,993,049 | 11/1976 | Kater | 128/640 |
| 4,066,078 | 1/1978 | Berg | 128/641 |

FOREIGN PATENT DOCUMENTS 2814061 10/1978 Fed. Rep. of Germany ......................... 128/303.13

Primary Examiner—Lee S. Cohen
Attorney, Agent, or Firm—Irving Newman

[57] ABSTRACT

A grounding electrode useful in electrosurgery and easily contoured to body surfaces which comprises a flexible, perforated metal sheet, the lower side of which is coated with a conductive adhesive and the upper side of which is adhesively secured to a fenestrated film, said fenestrated film being adhesively secured to an open cell polymeric foam, and a conductive snap or button for conducting an electrical current secured to said metal sheet and extending through said fenestrated film and said polymeric foam.

Preferably, the metal sheet is aluminum foil, the conductive adhesive is a quaternary polymer and said open cell foam is polyurethane.

6 Claims, 2 Drawing Figures

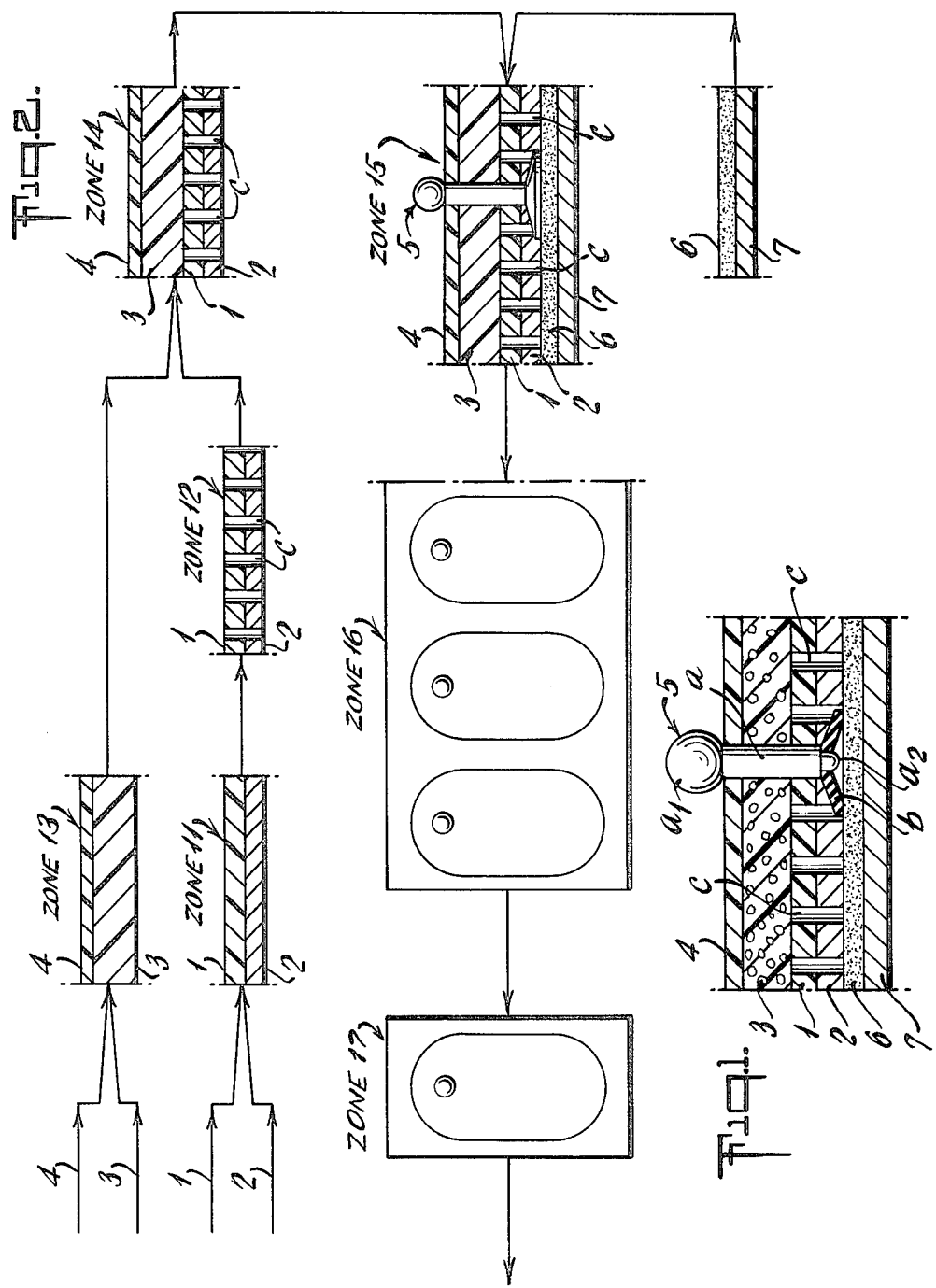

ELECTROSURGICAL GROUNDING PAD

FIELD OF THE INVENTION

The instant invention relates to electrosurgical grounding pads, i.e. grounding electrodes useful in electrosurgical procedures.

SUMMARY OF THE PRIOR ART

In electrosurgical procedures, e.g., cauterization, fulguration and electrocoagulation, a ground electrode is contacted with the patient to prevent burning, etc.

Meal plates or foil may be used as grounding electrodes; preferably the plate or foil is coated with an electrically conductive gel to insure grounding of the patient. This procedure is described in U.S. Pat. Nos. 3,960,141; 3,972,329; and 3,848,600.

The latter patent teaches the importance of insuring that the conductive area of the grounding electrode, which is in contact with the patient undergoing the electrosurgical procedure, is at least 9 square inches. Metal plates are, of course, nonconformable to the contours of the human body, therefore, problems in patient burns have occurred with such grounding electrodes. Foils are more conformable; however, in the prior art electrodes, an adhesive area is also required to insure that the foil will be maintained in proper body contacting relationship. An adhesive area is added which increases the overall area of the grounding pad electrode in contact with the patient without concomitant increase in conductive area.

Medical electrodes useful in monitoring and stimulating procedures are known wherein conductive adhesives have been utilized. However, these electrodes have much smaller areas of conductivity and are therefore, not suggested for use as electrosurgical grounding electrodes. See for example, U.S. Pat. Nos. 3,607,788; 3,565,049; 3,426,746; 3,845,757; 4,016,869; 4,008,721; 3,993,049 and 3,911,906.

In U.S. Pat. No. 4,066,078, an electrode is described which utilizes a quaternary polymer or a sulfated polymer as a conductive adhesive. While this patent discloses an electrode suitable for any medical use, it does not teach that the amount of absorbed moisture must be maintained between 6 and 20 weight percent of the quaternary polymer throughout the electrosurgical procedure, e.g., up to 8 hours, to insure adhesion of the electrode to the human body.

DESCRIPTION OF THE INVENTION

The instant invention relates to an electrosurgical grounding pad comprising an open cell foam, laminated to a fenestrated film, e.g., polyethylene, said film being adhered to a perforated metal foil, e.g., a aluminum, which is in turn coated over substantially the entire surface away from said film with an electroconductive polymer, e.g., a quaternary polymer(,) and an electrically conductive snap or button mechanically and electrically connected with said metal foil extending through the open cell foam said snap or button being adapted for connection to an electrosurgical device. Preferably, said foam is laminated at the surface away from said fenestrated polyethylene film to a woven fabric such as nylon tricot.

a. The Foam

The foam is necessary to impart proper feel to the electrosurgical grounding pad of the instant invention by contributing to the loft of the construction. The foam useful in preparing the instant novel electrosurgical grounding pad must be open celled to provide moisture transmission away from the conductive adhesive.

The foam may be a polyethylene, polyurethane, etc., examples of which are known in the art. The foam density may vary from 0.5 to 5 lb/ft$^3$ preferably from 1 to 3 lbs. per ft$^3$.

The foam is preferably hydrophobic so as not to retain the moisture which passes from the patient through the conductive adhesive.

It is critical that the electrosurgical grounding pad of the instant invention be conformable to parts of the human body where it is used, such as the leg or arm. Therefore, the foam must be flexible. A flexibility of from 0.2 to 10 psi as measured by the compressive stress at 10% deflection is desirable in the instant foams.

b. The Fenestrated Film

The fenestrated film contributes to the strength of the electrosurgical grounding pad of the instant invention(,) especially the strength of the connection between the snap and the metal foil, functions to support the foil during perforation, and bonds the foil to the foam. The fenestrated film may be polyethylene of thickness 0.00025" to 0.003" or another polymer having similar strength at said thickness. A paper or other nonwoven also may be utilized as the fenestrated film. However, additional adhesive must be used in bonding the paper to the foil and the foam. In the preferred embodiment, the fenestrated film is perforated with said perforations being registered through the perforations of the metal foil.

c. The Metal Foil

The metal foil provides conductivity between the conductive adhesive and the snap. Most any metal foil which is suitable to conduct the current required during electrosurgical procedure may be used. However, very high modulus of elasticity foiles (e.g. stainless steel) would detract from conformability and therefore are not preferred. Generally, aluminum foil is the material of choice. The aluminum foil will have a thickness of from 0.00025" to 0.003", preferably from 0.00025" to 0.001".

d. The Conductive Adhesive

The conductive adhesive is any conductive material which will bond to the metal foil and to the human body and is compatible with the patient's skin. These adhesives are known in the art and include the adhesives described in U.S. Pat. Nos. 3,845,757; 4,016,869; 4,008,721; 3,565,049 and 3,911,906 herein incorporated by reference for the purpose of describing the adhesive. These materials can be loaded with salts such as NaCl, $Na_2SO_4$, $K_2SO_4$, etc. or conductive particles such as carbon, alumina, etc. The most preferred embodiment for use in the electrosurgical grounding pad of the instant invention is described in U.S. Pat. No. 4,066,078 herein incorporated by reference for that purpose. The adhesives of U.S. Pat. No. 4,066,078 may be present in thicknesses of from 0.001" to 0.030" and at such thicknesses will meet the criteria of providing less than 700 ohms at electrosurgical grounding frequencies (primary frequency) of 25 kilohertz to 5 megahertz. The conductive adhesives of U.S. Pat. No. 4,066,078 are preferred over the aforementioned conductive adhesives because they are unfilled and unsalted materials. It has been found that materials containing fillers and(,) salts in general have a lower degree of adhesion to the human body and therefore, tend to lower the adhesion function during the long electrosurgical procedures in which the grounding pad is used. Furthermore, the conductive adhesives of U.S. Pat. No. 4,066,078 are hydrophilic in nature and transport water away frm the human body. The layers of hydrophobic conductive adhesives disclosed in the above referenced patents, must be perforated to provide pathways for the removal of water. This cuts down the effective conductive area. It has been found that the especially preferred quaternary homopolymer adhesive e.g., the homopolymer of an ester of an $\alpha,\beta$-olefinically unsaturated carboxylic acid and a monohydric alcohol having a terminal quaternary ammonium group(,) when plasticized with from 15% to 25% by weight of a polyhydric alcohol such as glycerol(,) gives the best balance of adhesive and conductive properties. These materials are especially suitable for use in the electrosurgical grounding pad of the instant invention when the moisture content thereof is maintained between 6 and 20 weight percent based on the conductive adhesive. Therefore, it is important that the preferred construction include sufficient perforations per square inch in metal foil and film when this adhesive is utilized as the conductive adhesive so that moisture may be transmitted away from the adhesive. Generally, 110 to 120 perforations of 0.045" diameter, per inch$^2$ will be suitable to provide from about 18 to 20% open area in the foil and film laminate. This degree of openness is suitable to maintain the above moisture content in the adhesive.

e. The Snap

The snap functions to mechanically and electrically connect the aluminum foil to the electrosurgical apparatus as shown. For example, in FIG. 1, the snap may comprise an eyelet and post construction. The eyelet is located under the aluminum foil and the post is attached thereto by punching through the construction into the eyelet and crimping said eyelet to the post to form an electrically integral connection. The material of choice for said post is nickel coated brass which is harder than aluminum and is easily fabricated. Because of its conductivity and compatability properties, the eyelet is preferably aluminum. Copper is also suitable except for use in conjunction with the preferred quaternary adhesive homopolymer, since it has been found to discolor said polymer and thereby detract from the appearance of the electrosurgical grounding pad of the invention. The post is an open cylinder having sharp edges. This form of construction provides a self piercing feature and is preferred since it minimizes the insulation of the post from the eyelet by the electrosurgical grounding pad materials during the connection of the post and the eyelet.

f. The Woven Fabric

The woven fabric contributes to the conformability of the electrosurgical grounding pad of the instant invention while providing strength to the construction and minimizing the extensibility of the foam. The fabric also contributes to the esthetic quality of the construction. It is preferred that a fabric having a biaxial stretch be used although a unilaterally stretchable fabric can be used when such stretch is in the long dimension of the fabric. It is important that the fabric be conformable since, when wrapping a limb, the outer layer must not buckle and thereby reduce the contact of the conductive adhesive below. Preferably, the fabric is a nylon tricot.

BRIEF DESCRIPTION OF THE FIGURES

FIG. 1 describes a preferred embodiment of the instant invention.

FIG. 2 describes a method of making said preferred embodiment.

DETAILED DESCRIPTION OF FIGURE 1: THE PREFERRED EMBODIMENT OF THE INSTANT INVENTION

Starting with the lower surface of the instant electrosurgical grounding pad construction (7) represents a release paper which is used to protect adhesive layer (6) prior to affixing said electrosurgical grounding pad to the body of a patient. Preferably, adhesive layer (6) comprises a homopolymer of a quaternary monomer such as described in U.S. Pat. No. 4,066,078. The adhesive is in turn secured at the surface away from the release paper to a perforated aluminum foil (2). The aluminum foil is secured by means of a extrusion bonded, low density, polyethylene adhesive to a fenestrated polyethylene film (1). The perforations (c) extend through both said polyethylene film and said aluminum foil in registered relationship. An open cell polyurethane foam (3) is laminated to said polyethylene film. A tricot nylon fabric (4) is laminated to said polyurethane foam and comprises the upper surface of the instant electrosurgical grounding pad. Extending through said fabric (4), foam (3), film (1) and foil (2) layers is a snap (5) which is suitable for electrically and mechanically connecting the instant electrosurgical grounding pad to an electrosurgical apparatus via a cable or wire. Snap (5) comprises a post (a) having a ball portion (a$_1$) extending above said tricot nylon layer and a self piercing end (a$_2$) located distally therefrom. The piercing end is useful for puncturing the above noted layers and may be crimped onto eyelet (b) which abuts the lower surface of said aluminum foil thereby providing electrical contact between the said aluminum foil and said ball (a$_1$). The post is made from nickel-coated brass and the eyelet is aluminum.

DETAILED DESCRIPTION OF FIGURE 2: THE CONSTRUCTION OF THE PREFERRED EMBODIMENT OF THE INSTANT INVENTION

Aluminum foil (2) and polyethylene film (1) are extrusion bonded in zone 11 to form a laminate. The film and the foil may be laminated by means of a polyethylene adhesive e.g., low density polyethylene. The laminate may be corona treated at the polyethylene surface to increase the polarity and yield a stronger bond from the subsequent flame lamination process. The corona treated laminate is perforated in zone 12 by means of a perforating machine. A urethane foam (3) is laminated to a tricot nylon fabric (4) in zone 13 and said laminate is bonded to the perforated laminate from zone 12 in zone 14. As shown, the foam is laminated to the perforated polyethylene film by a flame lamination process. To the laminate from zone 14 is affixed a conductive metal snap (5), said snap, as described above, being a two piece construction having a self piercing post for piercing said laminate and an eyelet which engages said post and the lower surface of said aluminum foil. The eyelet is set toward the edge of said laminate and the post is driven through the laminate and crimped into the eyelet. The laminate is coated at the aluminum foil surface in zone 15 with a conductive adhesive film (6) such as the homopolymer of a quaternary polymer. The conductive adhesive film (6) is carried to said zone supported on release paper (7). Electrosurgical grounding pads measuring approximately 20 square inches are punched out of the above laminate by die cutting to the release paper in zone 16. Finally, individual grounding pads ready for packaging are cut by means of a guillotine knife in zone 17.

What is claimed is:

1. A grounding electrode useful in electrosurgery and easily contoured to body surfaces which comprises:
   an open cell polymeric foam;
   a flexible, perforated metal sheet having an upper side and a lower side;
   a fenestrated film having first and second sides;
   and electrically conductive means adapted to be connected to an electrosurgical device for conducting an electrical curreent therefrom; said lower side of said metal sheet being coated with a conductive adhesive, said upper side of said metal sheet being adhesively secured to said first side of said fenestrated film, said polymeric foam being adhesively secured to said second side of said fenestrated film, and said conductive means being secured to said metal sheet and extending through said fenestrated film and said polymeric foam.

2. The electrode of claim 1 wherein said metal sheet is aluminum.

3. The electrode of claim 1 wherein said means for conducting an electrical current comprises a snap composed of an aluminum eyelet secured to said metal sheet and a nickel coated brass post that extends beyond said polymeric foam and passes therethrough and through said film and is mechanically secured to said aluminum eyelet in electrical conducting relationship to said metal sheet.

4. The electrode of claim 1 wherein said conductive adhesive comprises a quaternary polymer.

5. The electrode of claim 1 wherein said foam is polyurethane.

6. The electrode of claim 1 additionally including a nylon fabric adhesively secured to said open cell foam at the surface away from said metal sheet.

* * * * *